United States Patent [19]
Pierce

[11] Patent Number: 5,908,426
[45] Date of Patent: Jun. 1, 1999

[54] SUTURE NEEDLE MANIPULATOR

[76] Inventor: Javin Pierce, 4780 Mountain Rd., Stowe, Vt. 05672

[21] Appl. No.: 08/842,482

[22] Filed: Apr. 24, 1997

[51] Int. Cl.⁶ .................................................... A61B 17/00
[52] U.S. Cl. ............................................................ 606/139
[58] Field of Search ................................... 606/139, 144, 606/145, 147, 148, 181, 182, 222–227

[56] References Cited

U.S. PATENT DOCUMENTS

| | | | |
|---|---|---|---|
| 5,015,250 | 5/1991 | Foster | 606/147 |
| 5,129,912 | 7/1992 | Noda | 606/139 |
| 5,201,743 | 4/1993 | Haber | 606/147 |
| 5,211,650 | 5/1993 | Noda | 606/139 |
| 5,304,184 | 4/1994 | Hathaway et al. | 606/144 |
| 5,304,185 | 4/1994 | Taylor | 606/147 |
| 5,376,096 | 12/1994 | Foster | 606/147 |
| 5,403,329 | 4/1995 | Hinchliffe | 606/147 |
| 5,433,722 | 7/1995 | Sharpe et al. | 606/148 |
| 5,458,609 | 10/1995 | Gordon | 606/144 |
| 5,540,705 | 7/1996 | Meade | 606/145 |
| 5,578,044 | 11/1996 | Gordon | 606/144 |
| 5,586,986 | 12/1996 | Hinchliffe | 606/147 |
| 5,601,575 | 2/1997 | Messamer | 606/147 |
| 5,628,757 | 5/1997 | Hasson | 606/148 |
| 5,649,939 | 7/1997 | Reddick | 606/148 |
| 5,662,663 | 9/1997 | Shallman | 606/139 |
| 5,713,870 | 2/1998 | Yoon | 604/174 |
| 5,746,753 | 5/1998 | Sullivan et al. | 606/147 |

FOREIGN PATENT DOCUMENTS

| | | | |
|---|---|---|---|
| 1240496 | 7/1960 | France | 606/139 |
| 321755 | 6/1957 | Switzerland | 606/139 |
| 649416 | 2/1979 | U.S.S.R. | 606/139 |
| WO 92/12674 | 8/1992 | WIPO | 606/139 |

*Primary Examiner*—Michael Buiz
*Assistant Examiner*—Vikki Trinh
*Attorney, Agent, or Firm*—Snell & Wilmer, L.L.P.

[57] ABSTRACT

A suture needle manipulating device having an elongated substantially cylindrical shaft. A slot for receiving a suture needle is configured in a distal end of the shaft, and a handle is suitably affixed to a proximal end of the shaft. In addition, the needle manipulating device includes a slidable sheath assembly affixed around the shaft and is configured to engage the suture needle when it is in an initial retracted position.

When the needle is in the retracted position, the device with the needle can be inserted through an endoscopic portal. Once through the portal, the surgeon can then place the needle in an active, suturing position by retracting the sheath and applying tension to a suture attached to the suture needle. By applying tension to the suture, the swaged portion of the suture needle is retracted into a hollow cannula in the shaft until the needle becomes secured therein. At this point, the suture needle is extended and ready for suturing.

9 Claims, 4 Drawing Sheets

SUTURE NEEDLE MANIPULATOR

TECHNICAL FIELD

The present invention relates, generally, to a surgical instrument for use in an endoscopic cannula, and, more particularly, to an apparatus for holding and manipulating a suture needle through an endoscopic cannula during surgery.

1. Background Art and Technical Problems

With laparoscopic and endoscopic surgery, the surgeon typically creates an incision in a patient's body near an area where the surgery is to occur. The surgeon then places an endoscopic cannula or portal into the incision, which allows the surgeon to insert various surgical instruments such as scissors, dissectors, retractors, biopsy instruments, or the like to perform diagnostic procedures and/or surgery inside the patient's body.

After the diagnostic procedure and/or surgery has been completed, it is often necessary to close incisions or repair tissue inside the patient's body. Unfortunately, because the surgeon is conducting the surgery through a relatively small access portal, it is often very difficult to manipulate the necessary suture needle inside the body.

Various different endoscopic needle manipulating crevices are currently known in the art. However, most of the currently known devices typically have a pair of opposing jaws positioned at the distal end of an elongated member which is inserted through the endoscopic portal. With many of these devices, one jaw is commonly held stationery while the opposing jaw is operated between an open and a closed position. In addition, with some of these known devices, the opposing jaws commonly include a plurality of teeth for further grasping the suture needle.

Some of these needle grasping devices currently known in the art include: U.S. Pat. No. 5,601,575 issued on Feb. 11, 1997 to Measamer et al.; U.S. Pat. No. 5,376,096 issued on Dec. 27, 1994 to Foster; U.S. Pat. No. 5,304,185 issued on Apr. 19, 1994 to Taylor; U.S. Pat. No. 5,201,743 issued on Apr. 13, 1993 to Haber et al.; and U.S. Pat. No. 5,015,250 issued on May 14, 1991 to Foster. One problem with these currently known suture grasping devices is that a surgeon often must reposition the needle within the grasping jaws before it is in a proper position to actually suture tissue. This can be difficult given the limited amount of space in the portal to manipulate or reposition the needle. Moreover, given the geometry of the needle and the manipulating device, it is often very difficult for the surgeon to reach and suture certain tissues in the body. Thus, surgeons have long been looking for a more versatile needle manipulating device.

Another type of endoscopic suturing device is shown in U.S. Pat. No. 5,586,986 issued on Dec. 24, 1996 to Hinchliffe, and U.S. Pat. No. 5,403,329 issued on Apr. 4, 1995 also to Hinchliffe. These devices include sharp needles or trocars on both ends of a suture. The needles are shuttled from one side of the device to another where they are alternately apprehended by corresponding jaws and forced through tissue by coaction of the jaws effectively passing the suture. However, these devices are limited by the small amount of tissue that can be penetrated by the needles, and are also limited by the topography of the tissue that they can reach. Moreover, these devices have no ability to suture around a corner, which is often needed in endoscopic surgeries.

2. Summary of the Invention

Accordingly, it is an advantage of the present invention that an improved endoscopic needle manipulating device be provided that overcomes the limitations of the prior art.

It is another advantage of the present invention to provide a needle manipulating device which eliminates the need for movable jaws to handle the needle.

It is yet another advantage of the present invention to have a needle manipulating device that shields the needle tip during insertion through an endoscopic cannula.

It is still another advantage of the present invention to have a needle manipulating device which can be configured to grasp the tip of a suture needle and pull it and a suture through tissue after the needle has been first partially penetrated through the tissue being sutured with the same device.

The above and other advantages of the present invention are carried out in one form by a suture needle manipulating device having an elongated substantially cylindrical shaft. A slot for receiving a suture needle is configured in a distal end of the shaft, and a handle is suitably affixed to a proximal end of the shaft. In addition, the needle manipulating device includes a slidable sheath assembly affixed around the shaft that is configured to engage the suture needle when the suture needle is in its initial retracted position.

In the retracted position, the device with the needle can be inserted through the endoscopic portal. Once through the portal, the surgeon can then place the needle in an active, suturing position by retracting the sheath and applying tension to the suture attached to the suture needle. By applying tension to the suture, the swaged portion of the suture needle is retracted into a hollow cannula in the shalt until the needle becomes secured therein. At this point, the suture needle is extended and ready for suturing.

BRIEF DESCRIPTION OF THE DRAWING FIGURES

The present invention will hereinafter be described in conjunction with the appended drawing figures, wherein like numerals denote like elements, and:

DETAILED DESCRIPTION OF PREFERRED EXEMPLARY EMBODIMENTS

The present invention relates, generally, to a surgical instrument for use in an endoscopic portal, and more particularly to an improved suture needle manipulating apparatus for placing a filament of suture around or through a structure in the body using an endoscopic portal.

Figure 1:
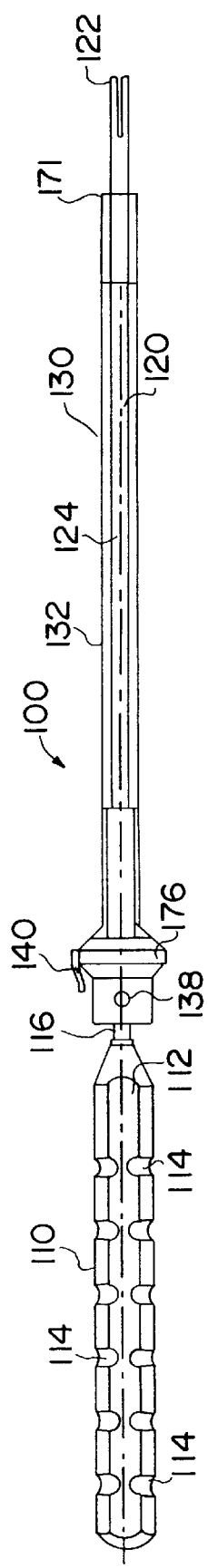
FIG. 1 is a side view of an exemplary suture needle manipulating device.

With reference to FIG. 1, an exemplary suture needle holding and manipulating device 100 is shown. In accordance with the present invention, needle manipulating device 100 suitably includes a handle 110, a shaft 120 and a needle securing sheath assembly 130.

Handle 110 may comprise any suitable endoscopic surgical instrument handle currently known or hereinafter developed. However, in accordance with the illustrated embodiment, handle 110 suitably includes a plurality of channels 112 (preferably 3) extending along the length of the handle, and a plurality of cut-out portions 114 uniformly spaced along the handle. Channels 112 and cut-out portions 114 are suitably configured to increase the frictional interface between the handle and a surgeon's hand, thus, improving the ability of the surgeon to adequately grasp the handle and, therefore, manipulate the device.

In addition, handle 110 may further include an extension 116 configured to removably attach to shaft 120 and sheath assembly 130. In accordance with this aspect of the invention, handle 110 may be detached from the needle manipulating device and used on a different surgical instrument. Also, with this configuration, a number of different types of endoscopic surgical handles may be attached to and used in conjunction with the needle manipulating device of the present invention.

Sheath assembly 130 is positioned around a large portion of, and is configured to slide along shaft 120. Accordingly, sheath assembly 130 suitably comprises a tube portion 132, a malleable distal end portion 134, a sheath handle 136 and a frictional drag assembly 138. As discussed in more detail below, sheath assembly 130 is configured to engage and secure a suture needle in a retracted position in needle manipulating device 100. In this regard, when sheath 130 is slid forward toward the distal end of shaft 120, malleable end portion 134 will encase a portion of the suture needle, holding it in its retracted position.

Malleable end portion 134 is fixedly attached to rigid tube portion 132, and is configured to deform or stretch when it engages the needle, so that it more firmly secures the needle therein. In accordance with this aspect of the invention, end portion 134 may be constructed from a number of different materials, however, in accordance with a preferred embodiment of the invention, end portion 134 is made from a malleable plastic or rubber material. In addition, rigid tube portion 132 may be constructed from a rigid thermoformed plastic or aluminum material.

Sheath handle 136 is connected to the proximal end of tube portion 132 of sheath assembly 130, and may comprise a variety of different configurations. For example, in accordance with the illustrated embodiment of FIG. 1, sheath handle 136 comprises an enlarged circular collar, which a surgeon may easily grasp and, thus, move along shaft 120. Sheath handle 136 may further include an adjustable frictional interface 138 which suitably comprises a finger screw passing through handle 136. The finger screw is a drag inducing device, which prevents sheath assembly 130 from sliding along the shaft when engaged. With this configuration, the surgeon can secure sheath 130 in a retracted or extended position, as necessary, without having to manually hold it in position.

While frictional interface 138 of the present invention is described as being a finger screw device, one skilled in the art will appreciate that frictional interface 138 may comprise any other suitable frictional drag device, such as, for example, a threaded clamp or the like.

Figure 11:
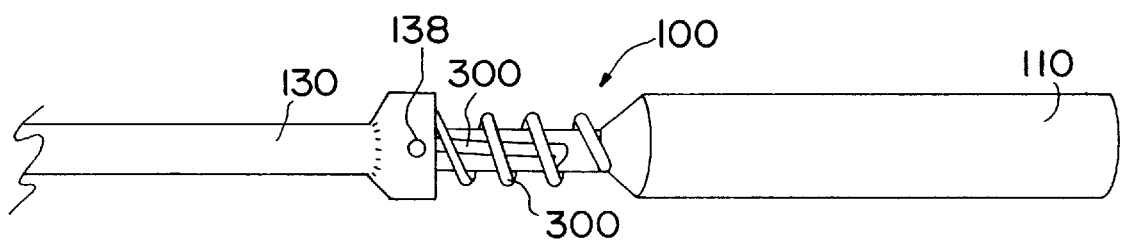
FIG. 11 is a side-view of yet another embodiment of a needle manipulating device having a spring and locking track assembly for controlling the movement of the sheath.

In addition, in accordance with a further embodiment of the invention, frictional interface 138 may be replaced by the locking mechanism illustrated in FIG. 11. In accordance with this aspect of the present invention, the illustrated embodiment of needle manipulating device 100 includes a spring 300 connected to sheath 130 and handle 110. Spring 300 is suitably configured to move sheath 130 to its extended engagement position; i.e., so that malleable end (not shown) engages the suture needle. Sheath 130 further includes a pin (not shown) which engages a slidable locking track 310 on shaft 120.

Figure 12:
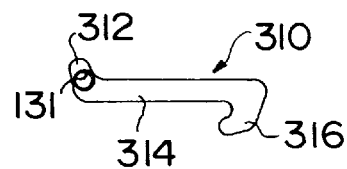
FIG. 12 is an expanded view of the locking track of FIG. 11.

As discussed above, when the surgeon wants to extend the suture needle into its engagement position, he retracts sheath 130 so that the malleable end portion exposes the suture needle. In accordance with the present embodiment of the invention, in retracting the sheath, the surgeon rotates sheath 130 so that the pin 131 attached to the sheath dislodges from position 312 of track 310 (see FIG. 12). As the sheath is retracted, the pin 131 follows the middle section 314 of the track. Finally, to lock the sheath in the retracted position, the sheath is rotated so that the pin 131 locks into section 316 of the track preventing the sheath from returning to the extended position.

Referring again to FIG. 1, attached to sheath handle 136 is a suture cleat 140 configured to receive and hold a suture in a tensioned position. Suture cleat 140 may comprise any suitable suture holding device, however, in accordance with the present invention, suture cleat 140 suitably comprises a small deformable tab of metal fastened to sheath handle 136. In accordance with this aspect of the invention, when a suture is slid under cleat 140, the cleat will slightly deform outward away from handle 136, pinching the suture between the cleat and the handle. With this particular configuration, a surgeon can quickly and easily secure and release a suture from the cleat.

Figure 2:
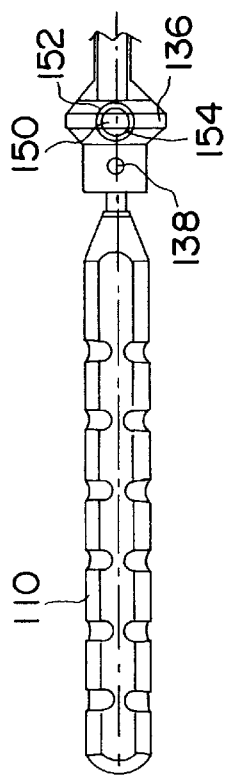
FIG. 2 is a side view of the handle and slidable sheath assembly of the device of FIG. 1, having an exemplary round suture cleat.

Referring now to FIG. 2, another embodiment of a suture cleat is illustrated. Specifically, an alternative suture cleat 150 may suitably comprise a circular plate 152 with a rubber washer 154 extending around the outer periphery of the plate. In accordance with this aspect of the invention, a suture is secured in cleat 150 by sliding the suture underneath rubber washer 154 so that the suture is secured between the washer and handle 136.

While the various embodiments of the suture cleat have been described herein as being connected to sheath handle 136, one skilled in the art will appreciate that the suture cleat may be positioned anywhere on device 100, such as, for example, on handle 110, or directly on sheath 130.

Moreover, while the preferred embodiment of the invention has been disclosed above as having a slidable sheath for encasing and protecting the needle during insertion, another embodiment of the invention may eliminate sheath 130. In accordance with this embodiment of the invention, the needle will simply dangle from needle receiving slot 160 as it is inserted through the endoscopic cannula.

Figure 3:
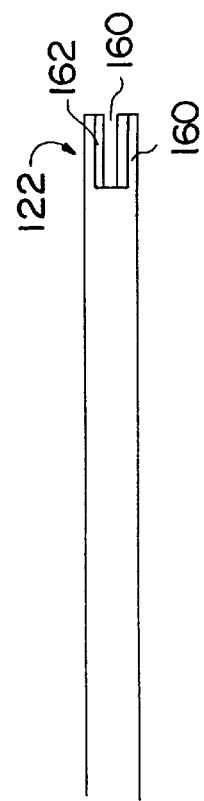
FIG. 3 is a top view of a distal end of the suture manipulating device of FIG. 1, showing a slot configured to receive and hold the suture needle.
Figure 4:
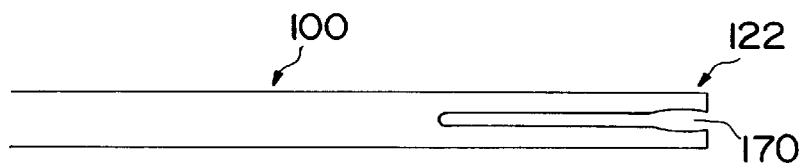
FIG. 4 is a bottom view of the distal end of the suture needle manipulating device of FIG. 1, showing a second groove configured to receive the suture connected to the suture needle.

Referring now to FIGS. 3 and 4, distal end 122 of shaft 120 and, in particular, needle receiving slot 160 (see FIG. 3) and suture receiving slot 170 (see FIG. 4) are illustrated. As discussed in more detail below, suture needle receiving slot 160 is suitably configured to secure a suture needle first, in a retracted position using sheath assembly 130 and second, in an extended suturing position. In the extended position, the surgeon can conveniently manipulate the needle to an appropriate suturing position. That is, the surgeon can pierce the needle through the tissue to be sutured at the appropriate location. In accordance with this aspect of the invention, needle receiving slot 160 suitably comprises a tapered edge 162 and a substantially flat edge 164, which inhibit lateral movement of the needle when it is in the extended position.

In addition to suture needle receiving slot 160, device 100 may suitably comprise a second slot 170 (see FIG. 4) for receiving the suture connected to the suture needle. Slot 170 allows the suture to pass outside the hollow cannula of shaft 120 so that the surgeon can have access to the suture without having to run the suture down the entire cannula and pass it out the end of the handle. However, while the preferred embodiment of the present invention includes suture receiving slot 170, a further embodiment of the invention may omit slot 170. In accordance with this aspect of the invention, the suture will be end passed through the device.

Figure 5:
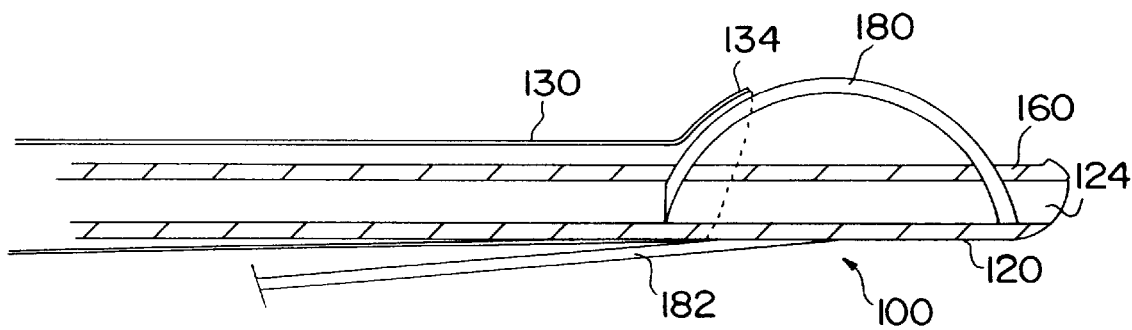
FIG. 5 is a cross-section view of the needle manipulating device of FIG. 1, showing the sheath assembly engaging the suture needle in its retracted position.

When the suture needle is in the retracted position, the tip of the needle will typically rest on a side of shaft 120 (see FIG. 5). In accordance with this aspect of the invention, shaft 120 may include an indentation for the needle to be secured within. In addition, in accordance with a further embodiment, shaft 120 may include a hole or slot for receiving the tip of the needle when it is in the retracted position. In any event, as discussed above, when the needle is in the retracted position, sheath 130 will typically cover the needle and secure it to that configuration.

Figure 6:
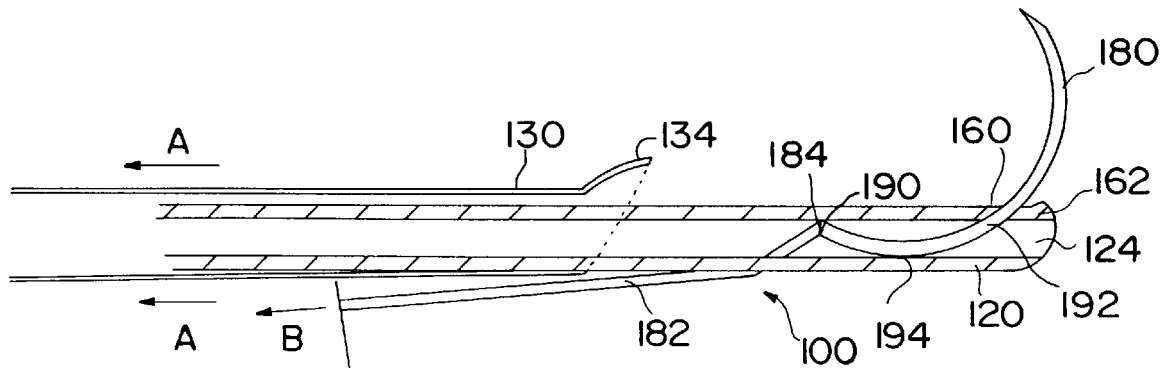
FIG. 6 is a cross-section view of the needle manipulating device of FIG. 1, showing the sheath assembly in a retracted position, and the suture needle in an engaged position.

Referring now to FIGS. 5 and 6, the operation of the suture manipulating device will now be discussed in more detail.

When inserting a suture needle 180 with a suture 182 through an endoscopic cannula, the needle is typically placed in a retracted position so that deformable end 134 of sheath 130 encapsulates or encases the tip of needle 180, preventing needle 180 from catching in the cannula or on tissue inside the body as it is inserted. To move suture needle 180 into its extended engagement position, sheath assembly 130 is first retracted back toward handle 110 as shown by arrows A in FIG. 6. In addition, either by retracting the sheath when the suture is attached thereto, or by separately applying tension to the suture after the sheath has been retracted, the surgeon will retract the suture in the direction illustrated by arrow B. The tension on suture 182 causes the swaged interface 184 between needle 180 and suture 182 to be retracted back into cannula 124 of shaft 120 until swagged interface 184 contacts the upper inner surface 190 of the cannula. When needle 180 is at this point, it is extended and secured in device 100 by three points of contact: upper inner surface 190 of cannula 124, the inside corner 192 of slot 160 and lower surface 194 of cannula 124. In accordance with this aspect of the invention, suture slot 170 is large enough so that suture 182 may slide down and out of the slot, but is small enough to prevent needle 182 from pulling through when tension is applied to the suture.

In addition to contact points 190, 192, 194, sides 162 and 164 of needle slot 160 are suitably configured to prevent the needle from spinning in the device when it is extended. However, because there is a relatively large tolerance between the needle and sides 162, 164, the needle will have some lateral movement within the device, allowing the surgeon to easily twist the needle to a desired angle so that he can reach awkward areas of the tissue.

After suture needle 180 has been extended to its engagement position, the surgeon will then secure suture 182 under suture cleat 140 so that the suture is secured. The surgeon will then insert needle 180 into and preferably through tissue at a suitable location. After the needle is inserted, the surgeon will then release suture 182 from suture cleat 140, allowing needle 180 to fall out the distal end of shaft 120. In accordance with this aspect of the invention, the surgeon will simply pull back on handle 110 of device 100 until needle 180 and suture 182 are freed from needle slot 160 and suture slot 170 respectively.

Figure 7:
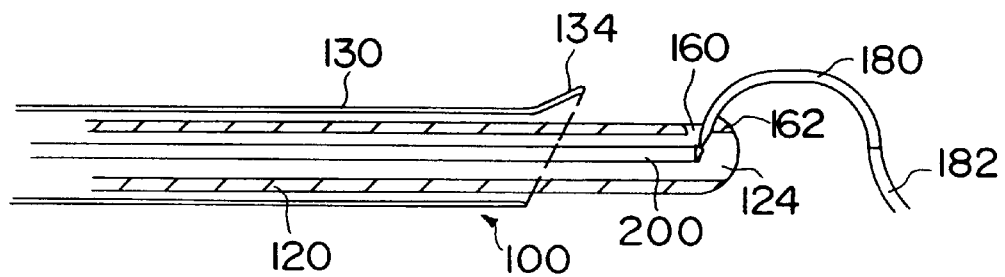
FIG. 7 is a cross-section view of a needle manipulating device having a plunger assembly for grasping and retrieving a suture needle.

After suture needle 180 has been suitably positioned within the tissue, it is often desirable to have a device that can grasp the tip of needle 180 and pull it and the suture through the tissue. Many times, the surgeon will insert a second endoscopic cannula near the first, so that a grasping instrument such as, tweezers or the like can suitably grasp and pull needle 180 through the tissue. In accordance with one aspect of the invention and referring now to two FIGS. 7 and 8, needle manipulating device 100 may be used in this manner. Specifically, needle manipulating device 100 may further include a plunger assembly 200 (see FIG. 7) which extends down cannula 124 of shalt 120 for grasping the needle. During the operation, the surgeon may position the tip of suture needle 180 within suture needle slot 160. The surgeon will then extend plunger 200 down cannula 124 until it contacts the tip of needle 180, pinching it between the end of the plunger and angled side 162. With this configuration, the surgeon can securely grasp the tip of needle 180 and pull it and attached suture 182 through the appropriate tissue. In accordance with a further aspect of this embodiment, plunger 200 may be used to urge the needle out of the distal end of the device to facilitate further penetration of the needle into the tissue.

Figure 8:
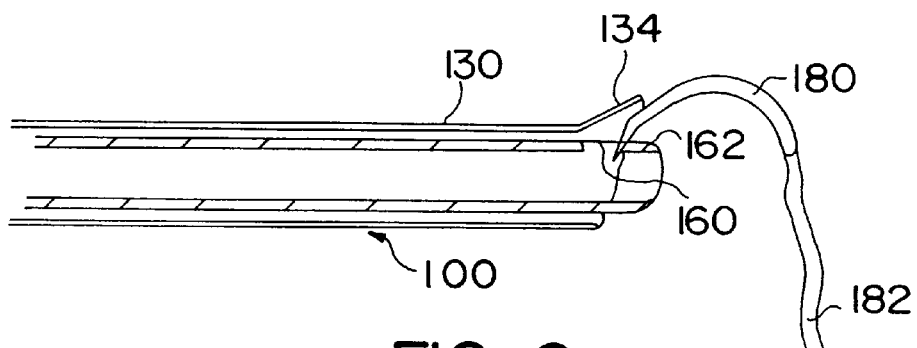
FIG. 8 is a cross-section view of a needle manipulating device in which the sheath assembly is used to grasp and retrieve a suture needle.

In accordance with a further embodiment of the present invention and referring now to FIG. 8, sheath assembly 130 may also be configured to grasp needle 180. In accordance with this aspect of the invention, the surgeon may suitably position the tip of needle 180 within needle slot 160, and extend sheath assembly 130 until deformable end 134 of sheath assembly 130 engages needle 180. At this point, deformable end 134 will encase a portion of needle 180 and, at the same time, pinch needle 180 against angled edge 162. As with the previous embodiment discussed above, the surgeon will have a firm grasp on the needle, so he can pull it and the attached suture through the tissue.

In accordance with yet a further embodiment of the present invention, to grasp and pull needle 180 through the corresponding tissue, suture needle slot 160 may be configured, so that when the tip of the needle is placed in slot 160, device 100 may be twisted or rotated until the tip is bound and secured in the slot. In accordance with this aspect of the invention, the surgeon can use the existing slot in device 100 to actually grasp and pull the needle through the tissue.

Figure 9:
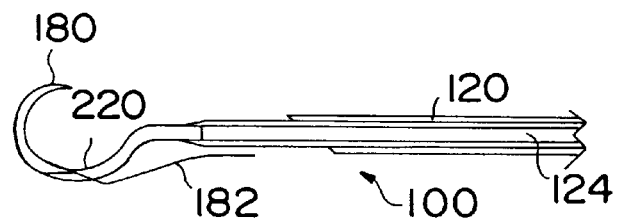
FIG. 9 is a side-view of a second embodiment of a needle manipulating device with a suture in an extended position.
Figure 10:
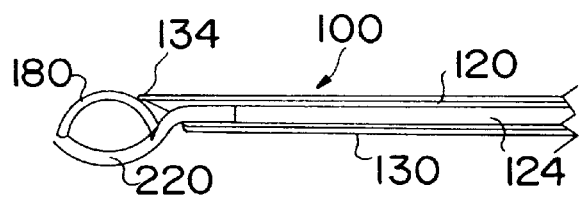
FIG. 10 is a side-view of the needle manipulating device of FIG. 9, with the needle in a retracted position.

Referring now to FIGS. 9 and 10, another embodiment of the present invention will be discussed. Specifically, shaft 120, as illustrated in the alternative embodiment of FIGS. 9 and 10, includes a curved distal end 220. In accordance with this configuration, needle 180 can be manipulated to reach certain tissues that otherwise would not be reachable; for example, the offset provided by the curved distal end enables the surgeon to access tissue that is obstructed to some degree by the topography of the body between the cannula and the site to be sutured. Also, this particular configuration, typically facilitates further penetration of needle 180 into the tissue being sutured. Finally, in accordance with another advantage of this configuration, the needle receiving slot 160 (FIG. 3) may be omitted because the curved end portion will prevent the needle from spinning or rotating in the cannula.

It will be understood that the foregoing description is preferred exemplary embodiments of the invention, and that the invention is not limited to the specific form shown or described herein. Various modifications may be made in the design, arrangement, and type of elements disclosed herein without departing from the scope of the invention as expressed in the appended claims.

I claim:

1. A suture needle manipulating device, comprising:

an elongated shaft having a proximal end and a distal end, the distal end of said shaft having a first slot on a first side of said shaft configured to receive a suture and a second slot on a second side of said shaft configured to receive a suture needle;

a handle rigidly affixed to the proximal end of said shaft; and a sheath slidably affixed around said shaft, said sheath configured to engage said suture needle in a retracted position when said sheath is extended, and further configured to release said suture needle when said sheath is retracted;

wherein said suture needle may be moved from said retracted position to an engagement position by retracting said sheath and applying tension to said suture attached to said suture needle.

2. The device as recited in claim 1, wherein said sheath further comprises a malleable distal end portion for securely engaging said suture needle in the retracted position.

3. The device as recited in claim 1, wherein said sheath further comprises a frictional drag interface configured to prevent said sheath from sliding along said shaft of said device.

4. The device as recited in claim 1, further comprising:

a spring fixedly attached between said handle and said sheath, said spring configured to keep said sheath in said extended position;

a guide slot in said shaft, said slot having a locking notch; and a pin connected to said sheath and configured to engage and follow said guide slot and lock within said locking notch;

wherein said sheath can be locked into a retracted position by moving said sheath toward said handle until said spring is at least partially compressed, and locking said pin into said locking notch.

5. The device as recited in claim 1, wherein said sheath comprises a suture cleat for securing a suture thereto.

6. The device as recited in claim 5, wherein said suture cleat comprises a deformable tab configured to pinch said suture between said tab and said sheath.

7. The device as recited in claim 5, wherein said suture cleat comprises a substantially circular disk having a rubber ring about the periphery of said disk and configured to pinch said suture between said rubber ring and said sheath.

8. The device as recited in claim 1, wherein said suture needle receiving slot comprises at least one tapered side configured for limiting the lateral movement of said suture needle in said receiving slot.

9. The device as recited in claim 1, further comprising a plunger extending along the bore of said shaft, said plunger configured for pushing said suture needle out of the distal end of said shaft.

* * * * *